United States Patent
Lewis et al.

(10) Patent No.: US 9,962,213 B2
(45) Date of Patent: May 8, 2018

(54) VARIABLE ANGLE DEPTH LIMITED FASTENER DRIVER AND VARIABLE ANGLE FIXATION SYSTEM FOR USE IN ORTHOPEDIC PLATES

(71) Applicant: ORTHOHELIX SURGICAL DESIGNS, INC., Medina, OH (US)

(72) Inventors: Derek S. Lewis, Copley, OH (US); Elizabeth Altenau, Lakewood, OH (US); Rebecca F. Kocher, Wadsworth, OH (US); Jackson R. Heavener, Warsaw, IN (US)

(73) Assignee: Orthohelix Surgical Designs, Inc., Medina, OH (US)

( * ) Notice: Subject to any disclaimer, the term of this patent is extended or adjusted under 35 U.S.C. 154(b) by 393 days.

(21) Appl. No.: 14/737,034

(22) Filed: Jun. 11, 2015

(65) Prior Publication Data
US 2015/0272649 A1 Oct. 1, 2015

Related U.S. Application Data

(62) Division of application No. 13/135,451, filed on Jul. 6, 2011, now abandoned.

(60) Provisional application No. 61/399,113, filed on Jul. 7, 2010.

(51) Int. Cl.
*A61B 17/88* (2006.01)
*A61B 90/00* (2016.01)

(52) U.S. Cl.
CPC ...... *A61B 17/8875* (2013.01); *A61B 17/8891* (2013.01); *A61B 90/03* (2016.02)

(58) Field of Classification Search
CPC .................. A61B 17/8875; A61B 17/8047
See application file for complete search history.

(56) References Cited

U.S. PATENT DOCUMENTS

| | | | |
|---|---|---|---|
| 2,940,488 A | 6/1960 | Riley, Jr. | |
| 3,146,811 A | 9/1964 | Shryock | |
| 3,527,273 A | 9/1970 | Falter | |
| 3,834,252 A | 9/1974 | Abell et al. | |
| 4,592,257 A | 6/1986 | Durr | |
| 4,762,035 A | 8/1988 | Fushiya et al. | |
| 5,101,698 A | 4/1992 | Paradiso | |
| 5,524,512 A | 6/1996 | Wolfe | |
| 5,797,918 A | 8/1998 | McGuire et al. | |
| 6,220,368 B1 | 4/2001 | Ark et al. | |
| 6,287,313 B1 | 9/2001 | Sasso | |
| 6,497,166 B1 | 12/2002 | Fleckenstein | |
| 6,547,013 B2 | 4/2003 | Riedl et al. | |

(Continued)

FOREIGN PATENT DOCUMENTS

| | | |
|---|---|---|
| WO | 2006102110 A1 | 9/2006 |
| WO | 2006103245 A1 | 10/2006 |
| WO | 2014145267 A1 | 9/2014 |

*Primary Examiner* — Andrew Yang
(74) *Attorney, Agent, or Firm* — Duane Morris LLP

(57) ABSTRACT

The present invention relates to an orthopedic fastener driver which can be used with a variable angle fixation system, and in particular in which the driver has a variable angle drive tip that is capable of screwing a fastener in an orthopedic plate assembly at a variable angle relative to the drive axis of the driver, and further wherein the driver has a drive mechanism including an interference clutch mechanism that disengages so as to limit the relative depth of the fastener in the plate assembly as to avoid driving the fastener or fastener assembly through the plate.

7 Claims, 4 Drawing Sheets

(56) References Cited

U.S. PATENT DOCUMENTS

| | | |
|---|---|---|
| 6,575,062 B2 | 6/2003 | Hahn |
| 6,647,836 B1 | 11/2003 | Habermehl |
| 6,830,574 B2 | 12/2004 | Heckele et al. |
| 7,052,499 B2 | 5/2006 | Steger |
| 7,197,968 B2 | 4/2007 | Bubel |
| 7,201,083 B2 | 4/2007 | Bader et al. |
| 7,255,703 B2 | 8/2007 | Mujwid et al. |
| 2006/0016300 A1 | 1/2006 | Bubel |
| 2006/0116678 A1 | 6/2006 | Impellizzeri |
| 2006/0155284 A1 | 7/2006 | Doherty et al. |
| 2006/0235400 A1 | 10/2006 | Schneider |
| 2008/0114359 A1 | 5/2008 | Muerner et al. |
| 2008/0119895 A1 | 5/2008 | Manceau |

VARIABLE ANGLE DEPTH LIMITED FASTENER DRIVER AND VARIABLE ANGLE FIXATION SYSTEM FOR USE IN ORTHOPEDIC PLATES

CROSS REFERENCE

This application is divisional application of pending U.S. patent Ser. No. 13/135,451, filed Jul. 6, 2011 which claims the benefit of priority under 35 U.S.C. § 119 of U.S. Provisional Application Ser. No. 61/399,113, filed on Jul. 7, 2010, herein fully incorporated by reference

FIELD OF THE INVENTION

The present invention relates to an orthopedic fastener driver which can be used with a variable angle fixation system, and in particular in which the driver is capable of screwing a fastener in an orthopedic plate assembly at a variable angle, and further wherein the driver has a drive mechanism that is limited by the relative depth of the fastener in the plate assembly so as to avoid driving the fastener or fastener assembly through the plate.

BACKGROUND OF THE INVENTION

As the understanding of the mechanics of bone stabilization and the corresponding constructs have become increasingly sophisticated, systems have been developed to allow for various types of fixation of orthopedic implants relative to the bone or bone fragments with which it is used. Initially, the fastener (typically a bone screw) simply rode in a screw hole and held a corresponding plate in compression to the bone fragments by virtue of the attachment between the fastener and the bone and the relationship between the fastener head and the fastener hole within the plate. However, as the field of internal fixation has developed, different approaches to fixation have also developed to accommodate locking fixation between the plate and fastener (in which the angle of fixation is designed to capture bone fragments from common break patterns and where the fastener is locked at that angle in the plate), variable angle fixation between the plate and fastener (in which the fastener could be fixed relative to the bone at a angle determined during surgery and where the fastener was able to move relative to the plate), and finally variable angle locking fixation (which includes a fastener assembly for which the fastener could be fixed relative to the bone at a variable angle, but could also be locked relative to the implant at that angle). This particular type of fixation allows for the biological and mechanical advantages of the previous two types of fixation, but is necessarily, the most complicated to achieve, in particular where it is of great advantage to have a fixation system that is easy to implant and which is designed to avoid malfunctions which could greatly complicate the surgery during which they are implanted.

The present invention provides a variable locking fixation system specifically including an orthopedic plate that has threaded fastener holes, which can receive a locking fixed angle screw having a head including threads that can mate with the threads of the locking holes. The fixation system further includes a variable angle locking assembly with a threaded locking insert that can be driven into the threaded locking holes of the plate. The locking insert is comprised of a material that is relatively deformable compared to the threads on the head of a variable locking fastener used in the variable locking assembly. The locking insert also includes an annular flange that surrounds the torque driving recess of the locking insert, and which resides on the top surface of the plate surrounding the fastener hole. This flange acts to help inhibit the possibility of the locking insert being driven through the plate during implantation. The fastener driver, in this case, a screwdriver, of the present invention further helps to inhibit this possibility, as well as the possibility of driving the screw too far within the locking insert, by providing a drive mechanism that will disengage at a determined depth. In particular, the screwdriver has a sleeve linked to a drive couple that disengages axially when the sleeve terminus encounters a surface, i.e. the top of the locking insert.

The screwdriver of the present invention further includes a replacement drive shaft and tip unit, which can be slide into position in the screwdriver drive body. This drive tip unit includes a variable angle drive tip that allows the screw to be inserted at the desired angle while permitting the body of the screwdriver to be used at a variable angle relative to the axis of the screw hole into which the screw is being inserted. This is of particular advantage where the screw may be difficult to access, and the room for maneuvering is small, such as is encountered in orthopedic surgery which involves the small bones, (i.e. those bones distal to the knee or elbow.)

SUMMARY OF THE INVENTION

The invention relates to a fastener driver which has a drive mechanism which includes a depth limiting feature that has an interference type drive clutch with a spring that biases the depth limiting assembly into engagement and that disengages when the fastener is inserted to a desired depth (in particular when the terminus of a depth limiting sleeve (joined by threads to a drive couple member) encounters a surface surrounding the fastener aperture which counters the bias of the spring to disengage the clutch assembly.

The fastener driver also includes a replaceable drive tip having a detent, which is preferably a coil spring that snaps into an annular groove within a drive feature housed within the depth limiting sleeve. The drive tip unit also includes a drive tip that floats within the driver tip unit at a variable angle to allow a fastener to be driver at an angle relative to the long axis of the drive train of the fastener driver. Specifically, the drive tip comprises a rounded end, which is advantageously a drive ball (i.e. a hex ball) or curving portion joined at ridges such that the cross-section of the rounded end of the tip in a plane transverse to the long axis forms a hex (although other geometries such as a pentagon or square or even a hexalobe could be used). The drive shaft of the drive tip unit includes a corresponding recess that has a shape including angles that are the inverse of the ridges of the drive ball that capture the drive ball to transmit torque to the drive end of the drive tip, which can be any appropriate geometry to correspond to the torque receiving recess of the fastener. In this case, the drive end is shown as a hexagon, but advantageously drive tip units can be supplied within a given system or surgical tray to accommodate various torque driving recesses, includes various sized hexagons, hexalobes, or even Phillips head fasteners.

In addition, the invention relates to a fastener system for use in orthopedic surgery which includes an orthopedic implant, such as an orthopedic plate having apertures that receives fasteners, and specifically includes variable locking apertures, in combination with a fastener driver that has a depth limiting feature, such as a clutch that disengages to inhibit the user from driving the fastener or fastener assembly too deep relative to the implant. Similarly, the invention relates to a method of promoting the achievement of variable angle fixation within an orthopedic plate comprising providing in an orthopedic tray, an orthopedic plate having a fastener aperture with an aperture axis, a fastener having a longitudinal axis which is capable of being implanted within said fastener aperture with its longitudinal axis at a variable angle relative to the aperture axis, and a fastener driver having a drive axis and which includes a mechanism that disengages to inhibit the fastener to be driven too deep relative to the plate, and optionally the fastener driver includes a variable angle drive tip that allows the tip to be used at a variable angle relative to the "drive axis" of the fastener driver (which is used herein to mean the long axis of the driver that defines the rotational axis through which the driver is driven).

The present invention achieves the foregoing goals within the fastener driver by providing a drive train comprising a drive shaft which is coupled to a handle for manual use or to a motor in the event that a power drive is desirable, and which has a housing for the shaft of a drive feature or linking section with a rectilinear (preferably having from 3 to 10 sides, and more preferably 4 to 8 or 6) boss section about an opening that houses the drive train, that forms an interference fit in a corresponding recess at the forward end of the drive couple. The drive feature further includes a second housing having a composite recess that accepts the end of a drive tip unit for easy replacement. A spring, which is preferably a coil spring, but could also include other biasing means, is biased between the front section of the first housing and at the other end against the rear end of a recess within a drive couple that has a front annulus including external threads that mate with the internal threads of a depth limiting sleeve which surrounds the second housing, as well as the drive tip unit up to the drive portion of the drive tip of the drive tip unit. The projecting drive portion of the drive tip unit engages the torque receiving recess of the fastener, and allows the fastener driver to be used to drive the fastener into an orthopedic plate. The sleeve has a terminal annular flat nose surrounding the drive tip, which will cause the drive train to uncouple by counteracting the spring to disengage the interference fit between the drive couple and the drive feature, essentially disengaging the clutch mechanism of the fastener driver of the present invention.

BRIEF DESCRIPTION OF THE DRAWINGS

The invention will be better understood and other features and advantages will become apparent by reading the detailed description of the invention, taken together with the drawings, wherein.

DETAILED DESCRIPTION OF THE DRAWINGS

The driver of the present invention is preferably intended for use in surgically implanting a bone fastener to a bone to retain the bone or bone fragment relative to an orthopedic implant, which could include various constructs such as cages, rods, and plates, but which is envisioned primarily for use with orthopedic plates. Similarly, the fastener with which the driver is intended for use could include various types of fasteners, such as screws and pegs (i.e. with and without bone threads), but for the sake of expediency, when the term "screw" is used herein, it should be interpreted to include fasteners without terminal threads, such as are sometimes referred to as pegs.

Further, the driver of the present invention is used advantageously with a variable angle or polyaxial fastener system in which the fastener, i.e. screw, is inserted into an aperture within the implant, i.e. plate, with its long axis at a variable angle relative to the central axis of the aperture. The present invention encompasses a plate/fastener system and method of enabling surgery which involves a plate having a threaded fastener aperture that accepts a variety of fasteners including a locking fastener having a threaded head which mates with the threads of the fastener aperture, or a variable angle non-locking fastener which has a partially spherical head that rides on the internal threads of the fastener aperture, or a variable angle locking assembly that includes a threaded locking insert that mates with the threaded fastener aperture and which comprises a material that will flow or deform relative to the threads of the head of a variable angle locking fastener that is threaded into the locking insert. Additionally, the present invention includes a fastener driver that has a depth limiting drive mechanism that will inhibit the user from driving any of these fasteners through the plate or too deep within the fastener aperture. The invention also relates to a method of enabling surgery comprising providing an orthopedic plate system that includes an orthopedic plate having at least one threaded fastener aperture, a fastener that can be threaded into the fastener aperture, and a fastener driver that includes a clutch that will disengage if the fastener is driven below a desired depth relative to the plate aperture. Where the plate allows for variable locking fixation using a locking insert as previously described, it should be understood that the locking insert could be considered to be part of the plate so as to define the fastener insert, or could be considered to be part of the fastener.

Figure 1:
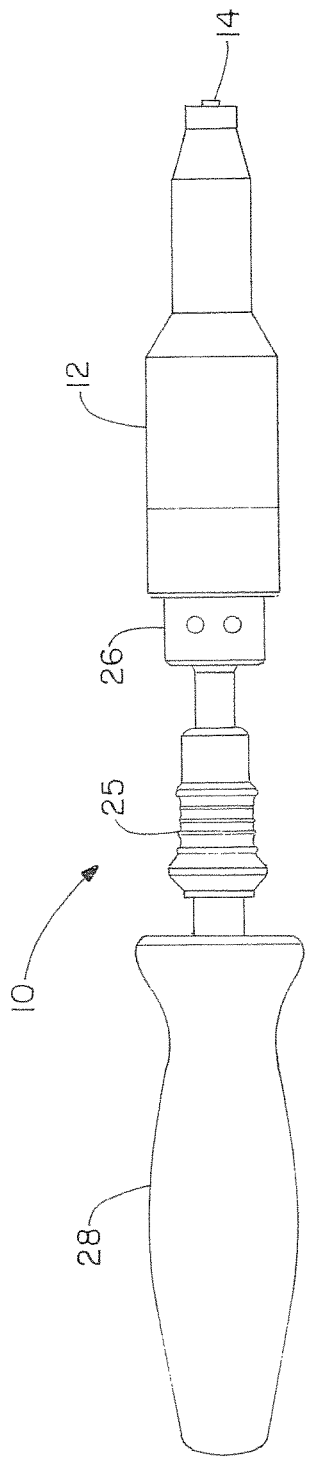
FIG. 1 is a side view of the fastener driver of the present invention.
Figure 2:
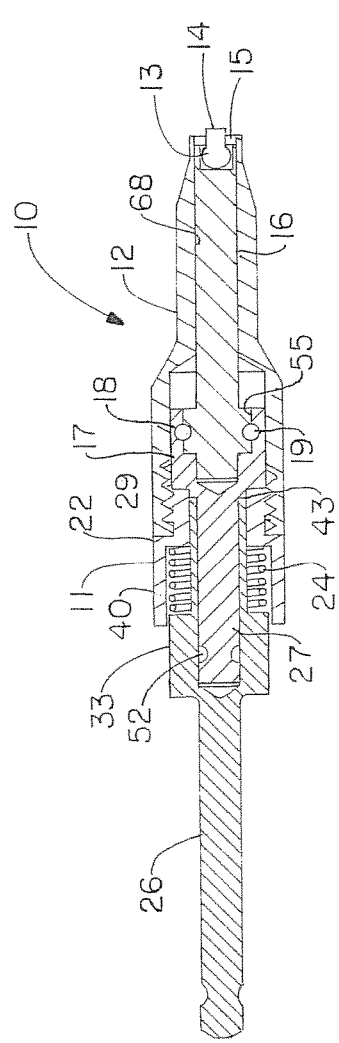
FIG. 2 is a cross section of the fastener driver shown in FIG. 1 taken along line 2-2.
Figure 3:
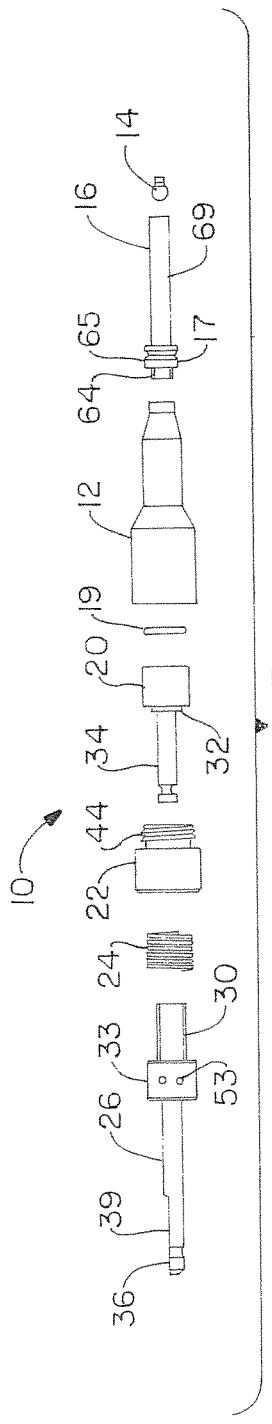
FIG. 3 is an exploded side view of the fastener driver of FIG. 1.
Figure 4:
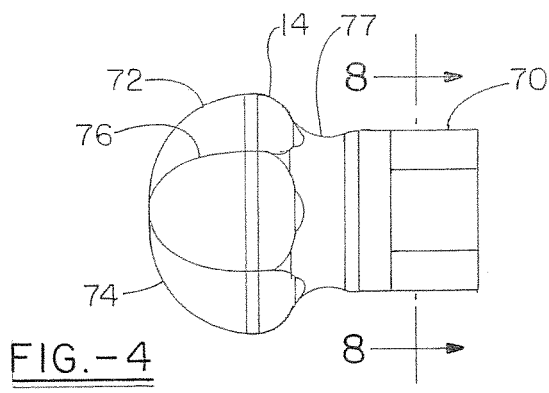
FIG. 4 is a first side view of a drive tip for use in the present invention.
Figure 6:
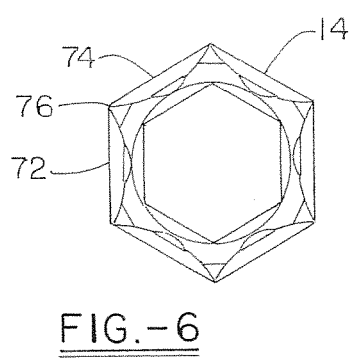
FIG. 6 is a first end view of the drive tip of FIG. 4.
Figure 5:
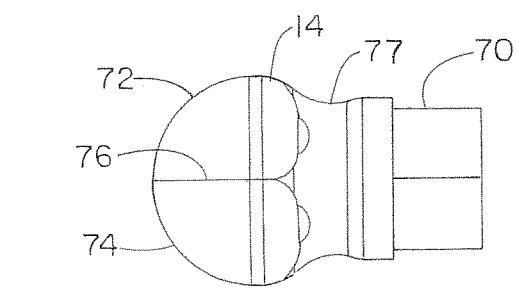
FIG. 5 is a second side view of the drive tip of FIG. 4 taken at a 90° radial rotation.
Figure 7:
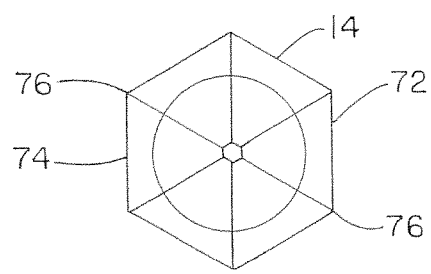
FIG. 7 is a second end view of the drive tip of FIG. 4.
Figure 8:
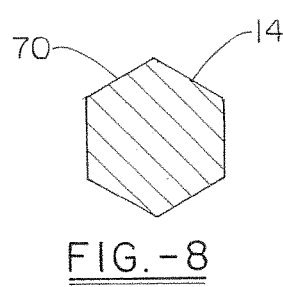
FIG. 8 is a cross section of the drive tip of FIG. 4 taken at line 8-8.
Figure 9:
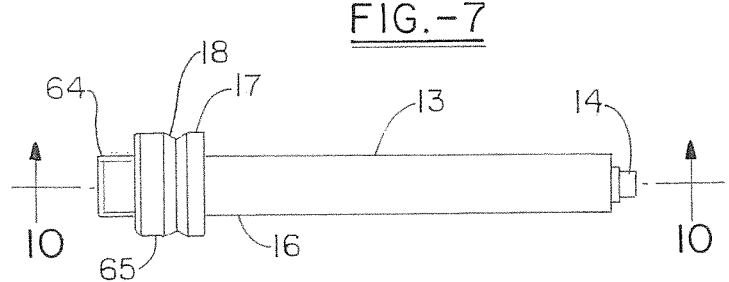
FIG. 9 is a side view of the replaceable drive tip unit of the present invention.
Figure 11:
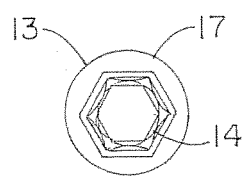
FIG. 11 is a first end view of the replaceable drive tip unit of FIG. 9.
Figure 10:
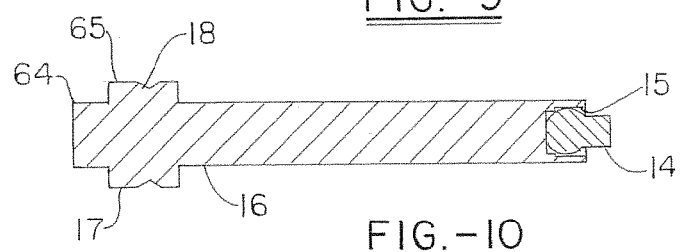
FIG. 10 is a cross section of the replaceable drive tip unit of FIG. 9.
Figure 12:
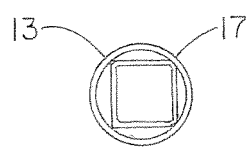
FIG. 12 is a second end view of the replaceable drive tip unit of FIG. 9.
Figure 15:
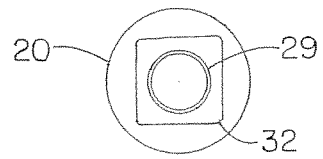
FIG. 15 is a first end view of the drive feature of FIG. 13.
Figure 16:
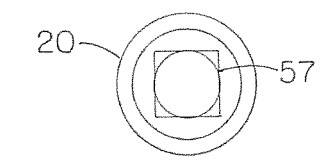
FIG. 16 is a second end view of the drive feature of FIG. 13.
Figure 13:
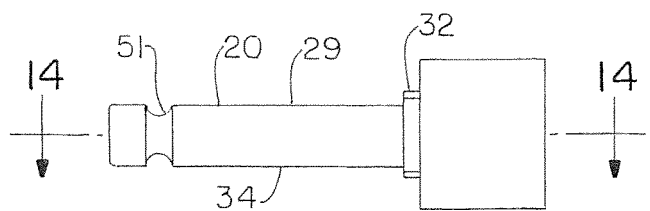
FIG. 13 is a side view of the drive feature of the present invention.
Figure 14:
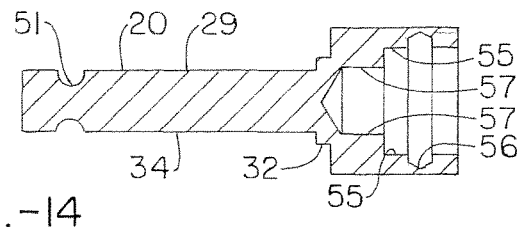
FIG. 14 is a cross-section of the drive feature of FIG. 13 taken along line 14-14.
Figure 17:
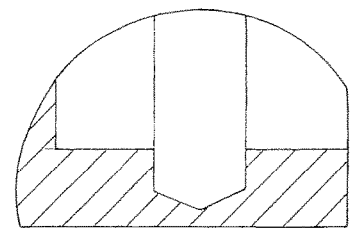
FIG. 17 is a detail of the annular groove within the drive feature of FIG. 13.
Figure 18:
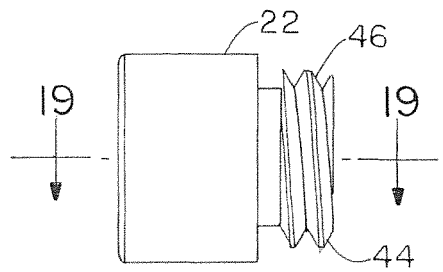
FIG. 18 is a side view of the drive couple of the present invention.
Figure 20:
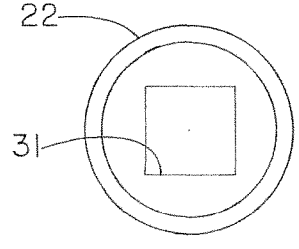
FIG. 20 is an end view of the drive couple of FIG. 18.
Figure 19:
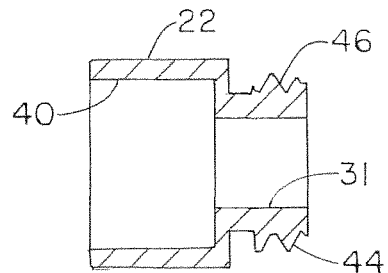
FIG. 19 is a cross-section of the drive couple shown in FIG. 18, and taken along line 19-19.
Figure 23:
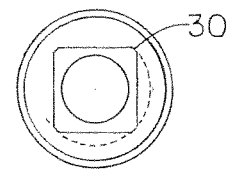
FIG. 23 is an end view of the drive connector of FIG. 21.

FIG. 1 illustrates a side view of the fastener driver of the present invention, which is further shown in cross-section is FIG. 2, and as an exploded view in FIG. 3. The driver 10 includes a disengageable drive mechanism 11 which includes a sleeve 12 that houses a replaceable drive tip unit 13. The replaceable drive tip unit 13 includes a drive tip 14, which is held in a recess 15 within a drive shaft 16. The drive shaft 16 is crimped around the rounded portion of the drive tip 14 so as to allow the drive tip to rotate in the recess 15, but to retain it axially from dislodging from the drive shaft 16. The drive shaft 16 has a shaft portion joined to a drive body 17, which includes a groove 18 that receives a detent spring 19.

The drive shaft 16 is removably inserted into and mechanically coupled (by means of an interference fit) to a compound recess within a drive feature or link 20 which is pinned within a drive connector 26. A drive couple 22 houses and mechanically couples the drive feature 20 with the drive connector 26 that is directly manually driven by means of the handle 28 shown as including an optional ratcheting mechanism 25. The drive connector 26 further includes a square shaft 30 which has the cylindrical recess 27 that receives the shaft portion 29 of the drive feature 20, and which is captured within the square recess 31 of the drive couple 22. The square recess 31 of the drive couple also accepts a square boss 32 on the rear face of the housing portion of the drive feature 20. It is this coupling between the square recess 31 of the drive couple 22 and the square boss 32 of the drive feature that transmits the drive torque to the drive tip unit 13, and ultimately drives the fastener.

The drive connector 30 also includes an annulus 33, which includes the terminus of the cylindrical recess 27 that accepts the cylindrical shaft 34 of the drive feature 20. Specifically, the shaft includes hollow section 51 that accommodate pins 52 held in pin openings 53 within the annulus 33 of the drive connector 26. This connection links the drive feature 20 both axially and radially to the drive connector 26.

A coil spring 24 is biased at one end against a front shoulder of the annulus 33 of the drive feature 26, and at the other end at the rear shoulder formed within a larger diameter recess 40 within the drive couple 22. The coil spring biases the drive couple 22 and the sleeve 12, which has a threaded connection to the drive couple forward relative to the drive feature (or in the direction toward the drive tip 14). The drive couple 22 has a front nipple 44 that includes external threads 46 that mate with the internal threads 50 within the bore of the sleeve 12.

The drive shaft 26 also includes a terminal shaft portion 36, which is adapted to be received within the recess 38 of the drive handle 28. One typical connection includes a flat 39 that permits the transmission of torque from the handle to the drive mechanism.

The axial play 43 between the square shaft 30 of the drive connector 30 and the correspondingly sized square boss 32 on the rear face of the drive feature within the square recess of the drive couple is what defines the disengagement of the drive mechanism, and forms the essence of the interference clutch mechanism of the fastener driver of the present invention.

The drive feature 20 has a compound recess 55 that includes an annular groove 56, which accepts a detent spring 18 to hold the replaceable drive tip unit within the fastener driver. The rear end 57 of the recess 55 is square and accepts a corresponding square drive shape 64 at the rear end of the drive shaft 16 of replaceable drive unit 13. Forward of the square section is a drive shaft body 65 which includes an annular groove 18 to also accommodates the detent spring 18 which is held within the groove 56 in the wider diameter portion of the compound recess within the drive feature.

The sleeve 12 includes an internal recess 68 that houses the drive feature 20 and the shaft 69 of the drive tip unit 13 and ends in an annular flat surface or nose 75. The shaft 69 of the drive tip unit includes a recess 15 that is hexagonal in cross-section so as to accept and transmit torque to the hex-ball section 72 of the drive tip 14. As is shown in FIGS. 4-8, the drive tip includes a section that includes rounded surface 74 that join at ridges 76 to permit the drive tip to be driven within the recess 15 of the drive tip unit and a necked portion 77 that accommodates the terminus of the recess 15. Thus, the drive tip can be driven at a variable angle of conical rotation relative to the drive axis of the fastener driver. The variable angle of conical rotation is from about 2° to about 30°, and preferably from about 5° to about 20°, and most preferably from about 7° to about 15°, since the tip is free to float on the rounded surfaces within the recess. The end 70 of the drive tip is a typical drive shape, and while it is illustrated as hexagonal, can encompass other drive shapes, including for example, hexalobe, star shape, square, and cross-shaped.

Figure 21:
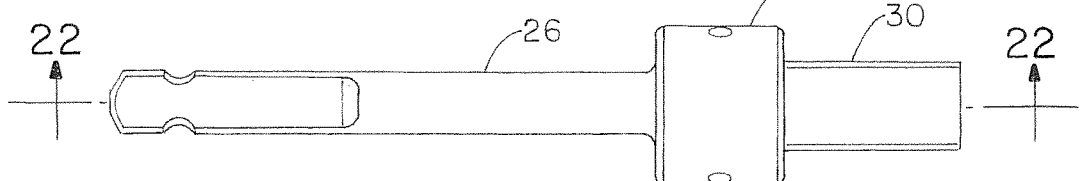
FIG. 21 is a side view of the drive connector of the present invention.
Figure 22:
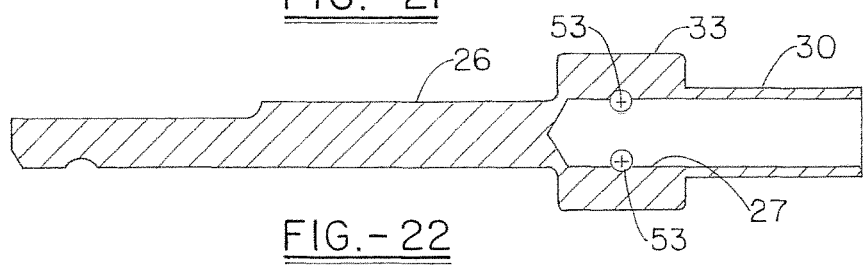
FIG. 22 is a cross-section of the drive connector shown in FIG. 21, and taken along line 22-22.
Figure 24:
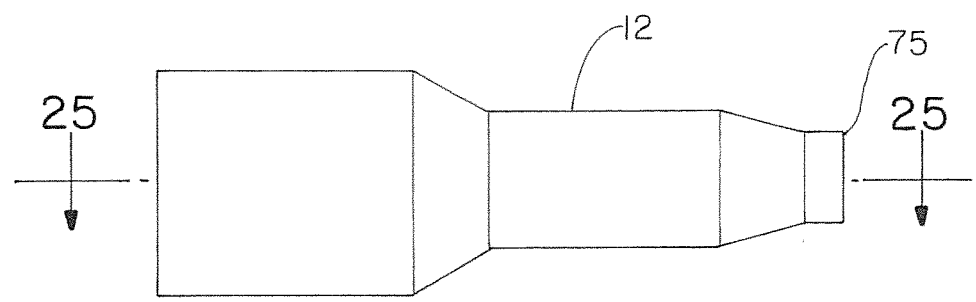
FIG. 24 is a side view of the depth limiting sleeve of the present invention.
Figure 25:
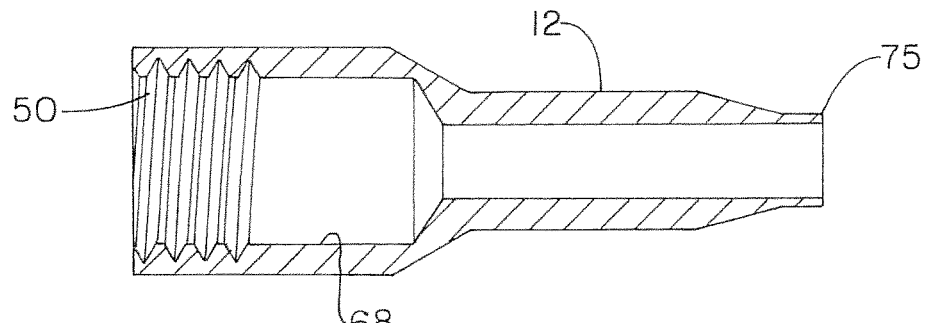
FIG. 25 is a cross-section of the depth limiting sleeve shown in FIG. 24, and taken along line 25-25.
Figure 26:
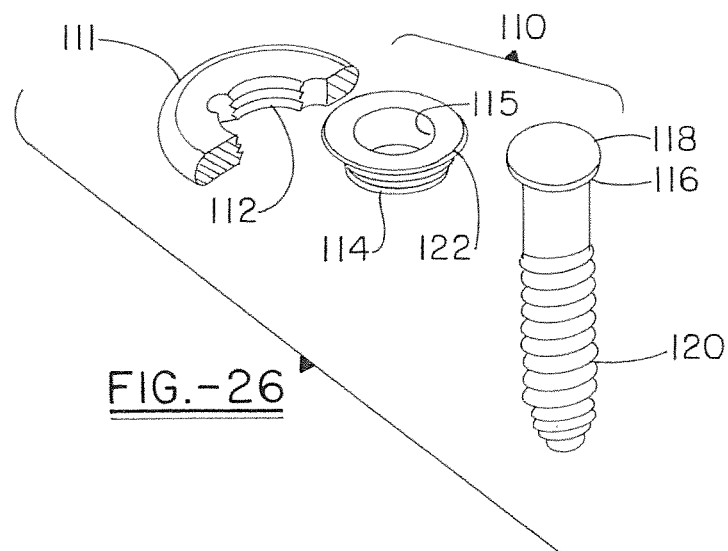
FIG. 26 is an exploded view of a variable locking assembly in accordance with a further aspect of the present invention with the plate illustrated in section

FIG. 21 illustrates a variable locking assembly with which the fastener driver of the present invention can be used. The locking assembly 110 includes an orthopedic plate 111 having one or more threaded fastener apertures 112 which accept a fastener having a head with corresponding threads or a locking insert 114, which has corresponding threads. The locking insert has an opening 115 that is shaped to allow the insert to be driven into the fastener aperture. One preferable shape is a modified hexagonal shape. Further the locking insert is made from a material (such as peek or nylon) that is biocompatible, and relatively can be deformed by the threads 116 on the head 118 of a variable angle locking fastener 120 that is threaded into the locking insert at a desired angle. The locking insert also preferably includes an annular flange 122 that surrounds the opening and which resides on top of the orthopedic plate surrounding the fastener aperture. In accordance with the present invention, the depth limited, variable angle driver is used to implant the fastener within the locking insert to avoid driving either the locking insert or the fastener too deep within the plate.

While in accordance with the patent statutes the best mode and preferred embodiment have been set forth, the scope of the invention is not intended to be limited thereto, but only by the scope of the attached claims.

What is claimed is:
1. A variable angle locking fixation system comprising:
an orthopedic plate system including
a plate having at least one fastener hole, a variable angle locking fastener which defines a variable angle locking fastener axis and having a head which has external threads and an internal torque driving recess, and a locking insert which engages the plate fastener hole and defines a fastener hole axis, the locking insert including an annular flange positioned on top of the orthopedic plate surrounding the fastener hole, the locking insert comprising a material deformable compared to the external threads on the head of the variable angle locking fastener; and a fastener driver having a drive shaft operatively aligned along a drive axis, the drive shaft including a drive tip having a torque driving section capable of mating with the internal torque driving recess of the variable angle locking fastener and further comprising a drive surface that can be positioned at a variable angle with respect to the drive axis so as to allow the fastener driver to drive the fastener with the drive axis or the variable angle locking fastener axis at an angle other than 0° relative to the fastener hole axis.

2. The variable locking fixation system of claim 1, wherein the locking insert is made of a material selected from the group consisting of PEEK or Nylon.

3. The variable locking fixation system of claim 1, wherein the fastener hole includes internal threads and the locking insert is threaded into the fastener hole.

4. The variable locking fixation system of claim 1, wherein the fastener driver further includes a drive mechanism that will disengage when the fastener reaches a predetermined depth relative to the plate fastener hole.

5. The variable locking fixation system of claim 1, wherein the drive shaft includes a drive recess and the drive tip comprises a plurality of drive ridges that are received in the drive recess.

6. The variable locking fixation system of claim 5 in which the drive tip comprises a hex-ball.

7. The variable locking fixation system of claim 1, wherein the fastener driver further comprises a sleeve.

* * * * *